United States Patent [19]

VandenBerg

[11] Patent Number: Plant 7,447

[45] Date of Patent: Feb. 12, 1991

[54] CHRYSANTHEMUM PLANT NAMED REDDING

[75] Inventor: Cornelis P. VandenBerg, Salinas, Calif.

[73] Assignee: Yoder Brothers, Inc., Barberton, Ohio

[21] Appl. No.: 388,892

[22] Filed: Aug. 2, 1989

[51] Int. Cl.[5] ..... A01H 5/00

[52] U.S. Cl. ..... Plt./82

[58] Field of Search ..... Plt./82

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Redding particularly characterized by its flat capitulum form, decorative capitulum type, red ray floret color, diameter across face of capitulum of up to 10 cm at maturity when grown as a pinched disbud pot mum, uniform nine week photoperiodic flowering response to short days, medium plant height when grown as a pinched pot mum, and spreading and prolific branching pattern.

3 Drawing Sheets

The present invention comprises a new and distinct cultivar of Chrysanthemum, botanically known as *Dendranthema grandiflora*, and referred to by the cultivar name Redding.

Redding, identified as 85-803002, was originated from a cross made by Cornelis P. VandenBerg in a controlled breeding program in Salinas, Calif., in 1985.

The female parent of Redding was the cultivar identified as Theme, disclosed in U.S. Plant Pat. No. 6,131. The male parent of Redding was an unnamed seedling identified as 82-051005.

Redding was discovered and selected as one flowering plant within the progeny of the stated cross by Cornelis P. VandenBerg in August of 1985, in a controlled environment in Salinas, Calif.

The first act of asexual reproduction of Redding was accomplished when vegetative cuttings were taken from the initial selection in October of 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Redding are firmly fixed and are retained through successive generations of asexual reproduction.

Redding has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Redding, which, in combination, distinguish this Chrysanthemum as a new and distinct cultivar:

1. Flat capitulum form.
2. Decorative capitulum type.
3. Red ray floret color.
4. Diameter across face of capitulum up to 10 cm at maturity, when grown as a pinched disbud pot mum.

5. Uniform nine week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum in a 15 cm pot.
7. Branching pattern is spreading and prolific.

The accompanying photographic drawings show typical inflorescence and leaf characteristics of Redding, with the colors being as nearly true as possible with illustrations of this type.

Sheet 1 is a color photograph of Redding grown as a pinched disbud pot mum grown in a 15 cm pot.

Sheet 2 is a black and white photograph of three views of the inflorescence of Redding.

Sheet 3 is a black and white photograph showing the upper and under sides of the leaves of Redding at three stages of development (mature, intermediate and immature).

Of the commercial cultivars known to the inventor, the most similar in comparison to Redding is the female parent Theme. Reference is made to attached Chart A, which compares certain characteristics of Redding to the same characteristics of Theme.

Similar traits are capitulum form and type, diameter across face of capitulum, plant height and flowering response. The ray floret color of Redding is a much brighter and deeper red than that of Theme which is greyed-red. Redding also has better color retention and a more prolific branching pattern than Theme.

In the following description color references are made to The Royal Horticultural Society Colour Chart. The actual color of ray florets of Redding is not represented in the RHS Colour Chart and the values given are those closest to the actual ray floret color. The color values were determined on plant material grown as a pinched disbud pot mum in Salinas, Calif. on Apr. 6, 1989.

Classification:

*Botanical*.—*Dendranthema grandiflora* cv Redding.

*Commercial*.—Decorative disbud pot mum.

INFLORESCENCE

A. Capitulum:

*Form.*—Flat.

*Type.*—Decorative.

*Diameter across face.*—Up to 10 cm at maturity.

B. Corolla of ray florets:

*Color (general tonality from a distance of three meters).*—Red.

*Color (upper surface).*—46A.

*Color (under surface).*—172B to 172C.

*Shape.*—Straight, flat, slightly ribbed.

C. Corolla of disc florets:

*Color (mature).*—1B.

*Color (immature).*—151C.

D. Reproductive organs:

*Androecium.*—Present on disc florets only; very few disc florets.

*Gynoecium.*—Present on both ray and disc florets.

PLANT

A. General appearance:

*Height.*—Medium; 25 to 35 cm as a pinched disbud pot mum with 0 to 7 long days after pinch prior to short days and 1 application of 2500 ppm B-9 SP.

*Branching pattern.*—Spreading and prolific.

B. Foliage:

*Color (upper surface).*—147A.

*Color (under surface).*—147B.

*Shape.*—Lobed and slightly serrated.

CHART A

COMPARISON OF REDDING AND THEME

| | REDDING | THEME |
|---|---|---|
| Ray Floret Color | Red | Greyed-red |
| Capitulum Form and Type | Flat decorative | Flat decorative |
| Branching Pattern | Spreading and prolific | Spreading |
| Diameter Across Face of Capitulum | Up to 10 cm | Up to 10 cm |
| Plant Height | Medium | Medium |
| Controlled Response | 9 weeks | 9 weeks |

Comparisons Made of Plants Grown As Pinched Disbud Pot Mums In Salinas, California

I claim:

1. A new and distinct Chrysanthemum plant named Redding, as described and illustrated.

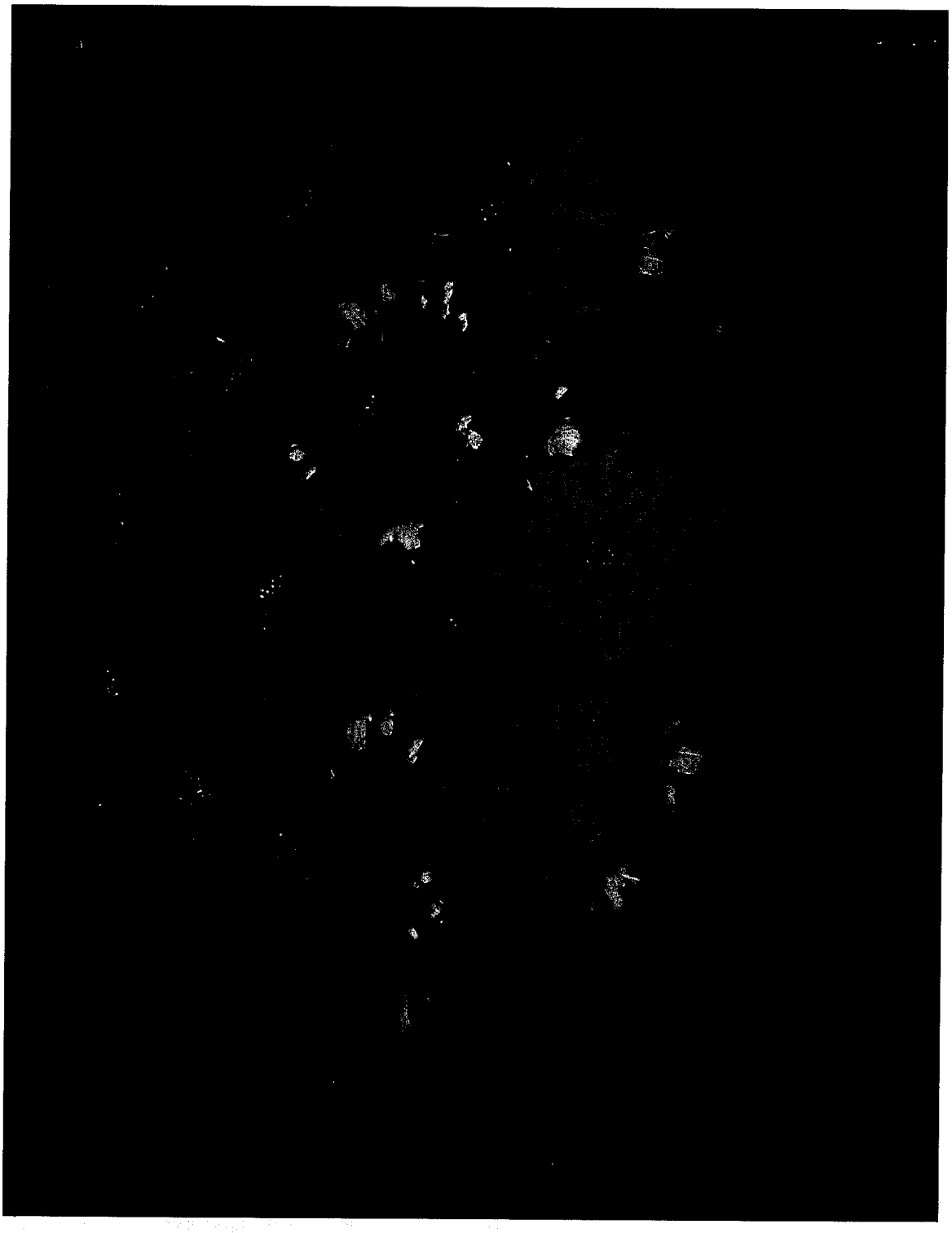

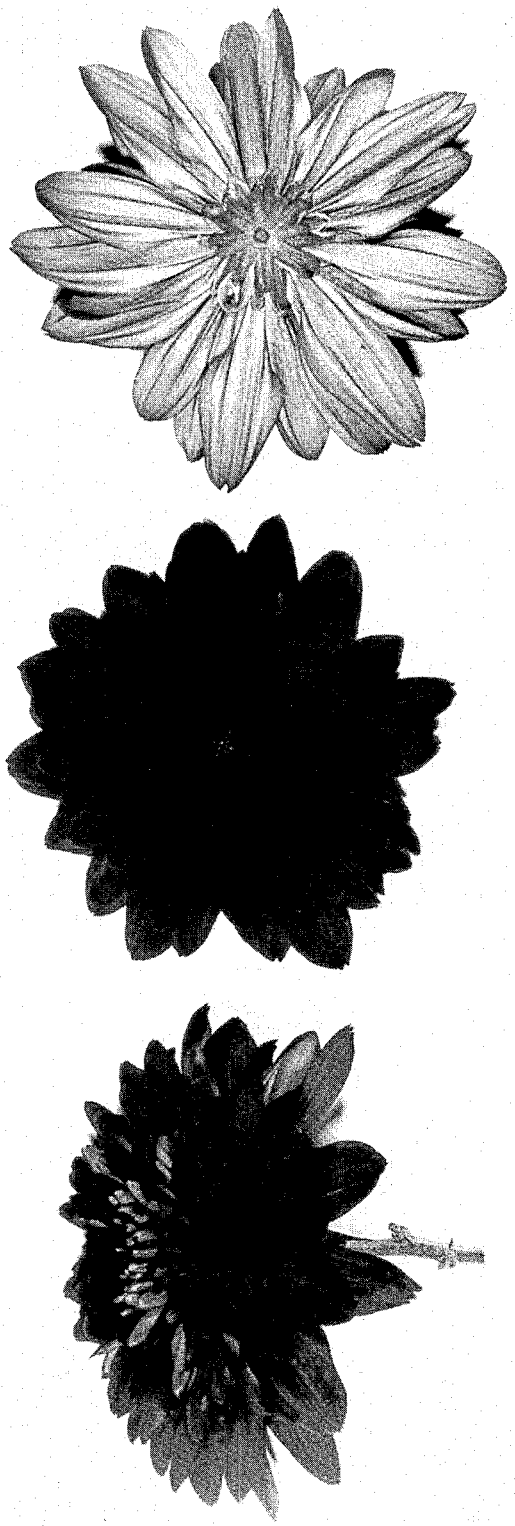

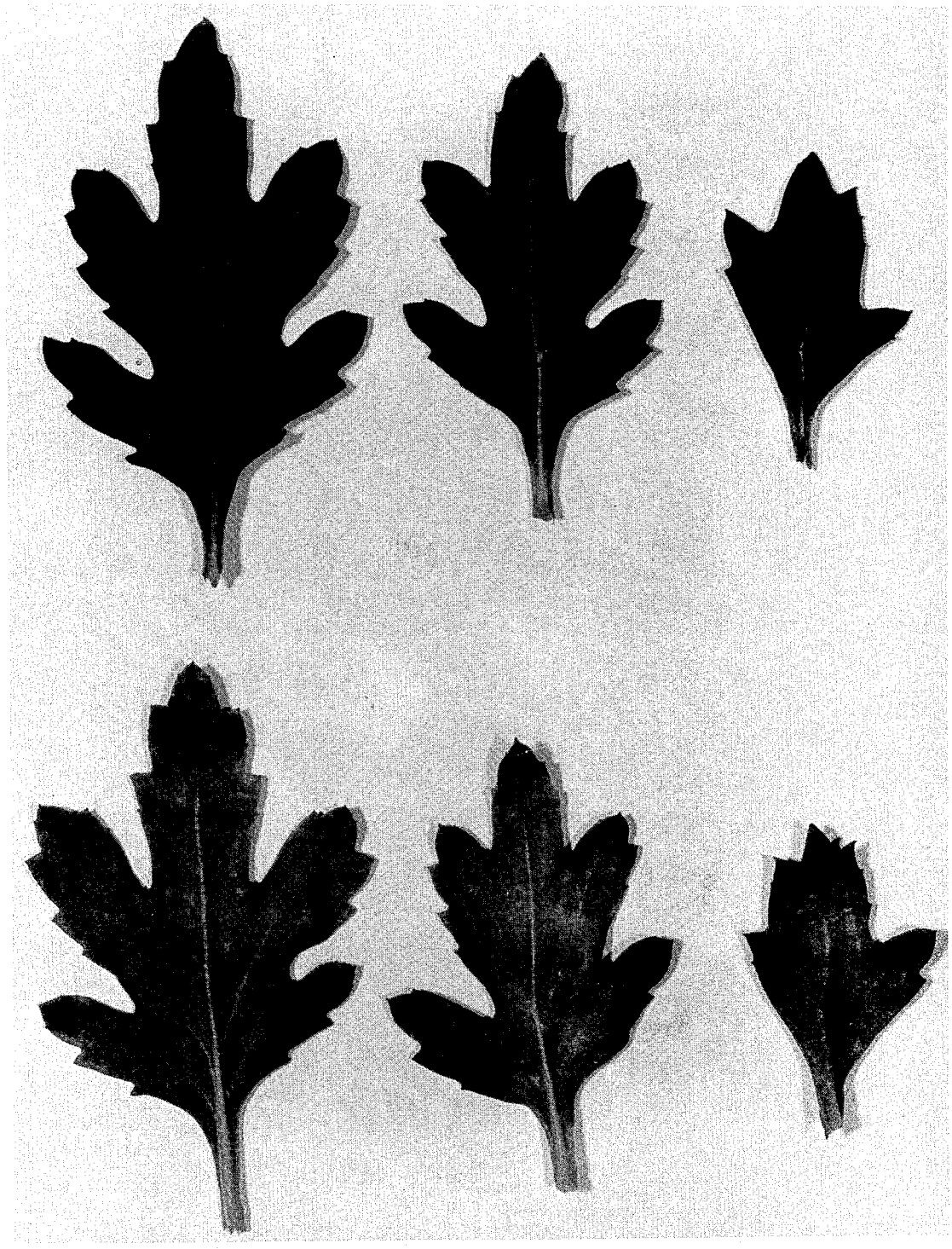

* * * * *